United States Patent
Livesey et al.

(10) Patent No.: US 8,895,236 B2
(45) Date of Patent: Nov. 25, 2014

(54) COMPOSITION FOR CRYOPRESERVATION COMPRISING NICOTINAMIDE, GLYCEROL AND RED BLOOD CELLS

(76) Inventors: Stephen A. Livesey, Eltham (AU); Michael Brian Burnett, Houston, TX (US); Jerome Connor, The Woodlands, TX (US); Christopher Todd Wagner, Houston, TX (US)

( * ) Notice: Subject to any disclaimer, the term of this patent is extended or adjusted under 35 U.S.C. 154(b) by 0 days.

(21) Appl. No.: 13/368,460

(22) Filed: Feb. 8, 2012

(65) Prior Publication Data

US 2012/0141974 A1 Jun. 7, 2012

Related U.S. Application Data

(60) Division of application No. 11/334,950, filed on Jan. 18, 2006, now abandoned, which is a continuation of application No. 09/623,846, filed as application No. PCT/US99/11674 on May 26, 1999, now abandoned.

(60) Provisional application No. 60/086,836, filed on May 26, 1998.

(51) Int. Cl.
*A01N 1/02* (2006.01)
*A61K 35/18* (2006.01)

(52) U.S. Cl.
CPC . *A01N 1/02* (2013.01); *A61K 35/18* (2013.01); *A01N 1/0226* (2013.01)
USPC .......................................................... 435/2

(58) Field of Classification Search
CPC .... A61K 31/16; A61K 35/18; A61K 2300/00
See application file for complete search history.

(56) References Cited

U.S. PATENT DOCUMENTS

| | | |
|---|---|---|
| 4,004,975 A | 1/1977 | Lionetti et al. |
| 4,018,911 A | 4/1977 | Lionetti et al. |
| 4,054,488 A | 10/1977 | Marbach |
| 4,327,799 A | 5/1982 | Scheiwe et al. |
| 4,531,373 A | 7/1985 | Rubinsky |
| 4,774,088 A | 9/1988 | Vora |
| 4,812,310 A | 3/1989 | Sato et al. |
| 5,043,261 A | 8/1991 | Goodrich et al. |
| 5,118,512 A | 6/1992 | O'Leary et al. |
| 5,153,004 A | 10/1992 | Goodrich, Jr. et al. |
| 5,242,792 A | 9/1993 | Rudolph et al. |
| 5,309,723 A | 5/1994 | Thomas et al. |
| 5,364,756 A | 11/1994 | Livesey et al. |
| 5,580,714 A | 12/1996 | Polovina |
| 5,601,972 A | 2/1997 | Meryman |
| 5,622,867 A | 4/1997 | Livesey et al. |
| 5,629,145 A | 5/1997 | Meryman |
| 5,750,039 A | 5/1998 | Brown et al. |
| 5,750,330 A | 5/1998 | Tometsko et al. |
| 5,759,764 A | 6/1998 | Polovina |
| 5,780,295 A | 7/1998 | Livesey et al. |
| 5,800,978 A | 9/1998 | Goodrich, Jr. et al. |
| 5,827,640 A | 10/1998 | Wiggins et al. |
| 5,897,987 A | 4/1999 | Oliver et al. |
| 5,919,614 A | 7/1999 | Livesey et al. |
| 5,958,670 A | 9/1999 | Goodrich, Jr. et al. |
| 6,007,978 A | 12/1999 | Goodrich, Jr. et al. |
| 6,037,116 A | 3/2000 | Wiggins et al. |
| 6,045,990 A | 4/2000 | Baust et al. |
| 6,059,968 A | 5/2000 | Wolf, Jr. |
| 6,114,107 A | 9/2000 | Wiggins et al. |
| 6,127,177 A | 10/2000 | Toner et al. |
| 6,176,089 B1 | 1/2001 | Bouche |
| 6,194,136 B1 | 2/2001 | Livesey et al. |
| 6,221,669 B1 | 4/2001 | Livesey et al. |
| 6,485,959 B1 | 11/2002 | Demetriou et al. |

FOREIGN PATENT DOCUMENTS

| | | |
|---|---|---|
| DE | 40 02 693 | 7/1991 |
| EP | 0 342 879 | 11/1989 |
| EP | 0 356 257 | 2/1990 |
| EP | 0 367 271 | 5/1990 |
| EP | 0 401 053 | 12/1990 |
| EP | 0 470 201 | 2/1992 |
| EP | 0 517 986 | 12/1992 |
| EP | 0 627 161 | 12/1994 |
| FR | 1 305 347 | 10/1967 |

(Continued)

OTHER PUBLICATIONS

Soszynski et al., "Effect of Protease Inhibitors on the Survival of In-Vitro Aged Erythrocytes", Cellular and Molecular Biology 33 (3) : 307-312 (1987).*
Aoyagi et al., "Leupeptins, new protease inhibitors from actinomycetes", J. Antibiotics 22 (6) : 283-286 (1969) abstract only.*
Hess, "Conventional blood banking and blood component storage regulation: opportunities for improvement", Blood Transfus. 8, Suppl.3: s9-s15 (2010).*
Angelini et al., "Evaluation of Four Different Methods for Platelet Freezing: in-vitro and in-vivo studies" Vox Sang 1992 vol. 2 No. 3, pp. 146-151.

(Continued)

*Primary Examiner* — Sandra Saucier
(74) *Attorney, Agent, or Firm* — McCarter & English, LLP; Matthew R. Van Eman; Vadim Cherkasov

(57) ABSTRACT

A red blood cell storage composition includes a composition of red blood cells and biochemistry altering reagents, the biochemistry altering reagents being present at a concentration so as to reduce the percent hemolysis of the red blood cells during the freeze-thaw cycle below that of the percent hemolysis of the red blood cells in the absence the biochemistry altering reagents. The red blood cell storage composition preferably includes reagents selected from: modifiers of glycolytic/metabolic components, modifiers of antioxidant potential, effectors of intracellular ionic distribution, modifiers of membrane fluidity, modifiers of cytoskeletal structure, effectors of the cyclooxygenase second messenger pathway, effectors of the lipoxygenase second messenger pathway, effectors of the hexose monophosphate second messenger pathway, effectors of the phosphorylation second messenger pathway, modifiers of specific messenger molecules, and combinations thereof.

10 Claims, No Drawings

(56) References Cited

FOREIGN PATENT DOCUMENTS

| | | |
|---|---|---|
| GB | 2330516 | 4/1999 |
| WO | WO 91/04659 | 4/1991 |
| WO | WO 91/18504 | 12/1991 |
| WO | WO 93/00806 | 1/1993 |
| WO | WO 93/14191 | 7/1993 |
| WO | WO 96/13158 | 5/1996 |
| WO | WO 96/24018 | 8/1996 |
| WO | WO 98/51147 | 11/1998 |
| WO | WO 99/60849 | 12/1999 |
| WO | WO 00/33653 | 6/2000 |

OTHER PUBLICATIONS

Arnold et al., "Photodegradation of Sodium Nitroprusside: Biologic Activity and Cyanide Release," Anesthesiology, 1984, vol. 61, No. 3, pp. 254-260.

Bayley, H., "Building Doors into Cells," Scientific American, Sep. 1997, pp. 62-67.

Beresewicz et al., "Erythrocyte membrane stabilization by calcium channel blockers, calmodulin antagonists and scavengers of oxygen free radicals," Polish Journal of Pharmacology and Pharmacy 42(4):355-364 (1990), Abstract.

Boutron, P. et al., "Reduction in Toxicity for Red Blood Cells in Buffered Solutions Containing High Concentrations of 2,3-Butanediol by Trehalose, Sucrose, Sorbitol, or Mannitol," Cryobiology, 1994, vol. 31, pp. 367-373.

Bowman et al., "Studies of the Recovery and the Cost of Low-Glycerol Cryopreserved Human Red Blood Cells," Transfusion, 1976, vol. 16, No. 2, pp. 113-121.

Brearley et al., "Nonmonotonic trends in electrolyte-induced injury to rapidly cooled erythrocytes," Cryobiology 29(2):175-182 (1992), Abstract.

Cook, J.R. et al., "Cold-Storage of Synthetic Human Epidermis in HypoThermosol," Tissue Engineering, 1995, vol. 1, pp. 361-377.

Daszynski et al., "Storage of Erythrocytes at Temperatures -20 to -24° C.," Acta Medica Polona, 1981, vol. 22, No. 2, pp. 151-160.

DeLoecker et al., "Effects of cell concentration on viability and metabolic activity during cryopreservation," Cryobiology 37(2):103-109 (1998), Abstract.

DeLoecker et al., "Osmotic effects of dilution on erythrocytes after freezing and thawing in glycerol-containing buffer," Cryobiology 30(3):279-285 (1983), Abstract.

Fagbemi et al., "Effect of Sodium Nitroprusside and L-Arginine Methyl Ester on Rat Hearts Stored at 4° C. for 24 h," Clinical Science, 1998, vol. 95, pp. 557-564.

Fujino et al., "Preharvest Nitroprusside Flush Improves Post-transplantation Lung Function," J. Heart Lung Transplant, 1997, vol. 16, pp. 1073-1080.

Funakoshi et al., "Neo Red Cell as an Organ Preservation Solution," Artificial Cells, Blood Substitutes, and Immobilization Biotechnology 25(4):407-416 (1997).

Goodrich, R.P. and Sowemimo-Coker, S.O., "Freeze-Drying of Red Blood Cells," in Advances in Low-Temperature Biology, 1993, vol. 2, Steponkus, P.L., Ed.; JAI Press LTD, London, pp. 53-99.

Greenwalt, T.J. et al., "The effect of Hypotonicity, Glutamine, and Glycine on Red Cell Preservation," Transfusion, 1997, vol. 37, pp. 269-276.

Gusev et al., "Effect of Metabolic Inhibitors on K+ Transport Across the Lamprey (*Lampetra fluviatilis*) Erythrocyte Membrane," Gen. Physiol. Biophys., 1994, vol. 13, No. 6, pp. 459-468.

Haas-Denk et al., "Beeinflussung der Thrombozytenfunktion und der Gerinnung von Konservenblut durch Azetylsalizylsa}re und Aprotinin" MED. WELT 28(19):912-914 (1977).

Hamasaki, N. et al., "Red Blood Cell Function and Blood Storage," Vox Sanguinis, 2000, vol. 79, pp. 191-197.

Högman, C.F., "Preparation and Preservation of Red Cells," Vox Sanguinis, 1998, vol. 74, No. 2, pp. 177-187.

Horn, E.-P. et al., "Transfusion of Autologous, Hyrdoxyethyl Starch-Cryopreserved Red Blood Cells," Anesth. Analg., 1997, vol. 85, pp. 739-745.

Jung et al., "Hypertonic Cryohemolysis: Ionophore and pH Effects," J. Membrane Biol., 1978, vol. 39, pp. 273-284.

Klebe R.J. and Mancuso, M.G., "Identification of New Cryoprotective Agents for Cultured Mammalian Cells," In Vitro, 1983, vol. 19, pp. 167-170.

Leibo et al., "Effects of Freezing on Marrow Stem Cell Suspensions: Interactions of cooling and warming rates in the presence of PVP, sucrose or glycerol," Cryobiology 6(4):315-322 (1970).

Luo, K. et al., "Effect of Dimethylsulfoxide and Hydroxyethyl Starch in the Preservation of Fractionated Human Marrow Cells," Cryobiology, 1994, vol. 31, pp. 349-354.

Mazur et al., "Contribution of unfrozen fraction and of salt concentration to the survival of slowly frozen human erythrocytes: influence of warming rate," Cryobiology 20(3):274-289 (1983), Abstract.

Mazur, P., "Freezing of Living Cells: Mechanisms and Implications," Am. J. Physiol., 1984, vol. 247, pp. C125-C142.

Mazur, "Physical and Chemical Changes During Freezing and Thawing of Cells, with Special Reference to Blood Cells," Bibl. Haemat 29(3):764-777 (1968).

Mazur et al., "Roles of unfrozen fraction, salt concentration, and changes in cell volume in the survival of frozen human erythrocytes," Cryobiology 26(1):1-29 (1989), Abstract.

McColm et al., "Comparison of fast (one-step) and interrupted slow cooling methods using a range of intracellular and extracellular cryoprotectants for the freeze-preservation of Plasmodium yoelii-infected mouse erythrocytes," Transactions of the Royal Society of Tropical Medicine and Hygiene 80(1):29-33 (1986), Abstract.

McGann, L.E. et al., "Manifestations of Cell Damage After Freezing and Thawing," Cryobiology, 1988, vol. 25, pp. 178-185.

Meryman et al., "Extending the Storage of Red Cells at 4° C.," Transfus. Sci., 1994, vol. 15, No. 2, pp. 105-115.

Meryman, H.T. "A Simplified Procedure for Deglycerolizing Red Blood Cells Frozen in a High Glycerol Concentration," Transfusion, 1977, vol. 17, pp. 438-442.

Moore et al., "Liquid storage at 4° C. of Previously Frozen Red Cells," Transfusion, 1997, vol. 27, No. 6, pp. 496-498.

Newman, Y.M. et al., "The Role of Trehalose and other Carbohydrates in Biopreservation," Biotechnology & Genetic Engineering Reviews, 1993, vol. 11, pp. 263-294.

Pellerin-Mendes et al., "In Vitro Study of the Protective Effect of Trehalose and Dextran During Freezing of Human Red Blood Cells in Liquid Nitrogen," Cryobiology, 1997, vol. 35, pp. 173-186.

Philipp et al., "Einfluss von Dipyridamol auf die Blutkonservierung," Acta Biol. Med. Germ., 1969, vol. 23, pp. 31-36.

Pinsky et al., "Cardiac Preservation is Enhanced in a Heterotopic Rat Transplant Model by Supplementing the Nitric Oxide Pathway," J. Clin. Invest., 1994. vol. 93, pp. 2291-2297.

Rittmeyer, I.C. et al., "Influence of the Cryoprotective Agents Glycerol and Hydroxyethyl Starch on Red Blood Cell ATP and 2,3-Diphophoglyceric Acid Levels," Vox Sanguinis, 1992, vol. 62, pp. 141-145.

Rodriguez et al. "Role of sodium nitroprusside in the improvement of rat liver preservation in University of Wisconsin solution: A study in the isolated perfused liver model," J. Surg. Res. 87(2):201-208 (1999), Abstract.

Rudowski et al., "Studies of Freezing of Outdated Erythrocyte Concentrates and Their Evaluation After Thawing," Acta. Medica Polona, 1978, vol. 19, No. 3, pp. 337-348.

Shier, W.T. and Olsen, S.G., "Isotonic Sucrose Improves Cryopreservation of Cultured Mammalian Cells," In Vitro Cell. Dev. Biol., 1995, vol. 31, pp. 336-337.

Smith et al., "Nitroprusside Produces Cyanide Poisoning via a Reaction with Hemoglobin," Journal of Pharmacology and Experimental Therapeutics, 1974, vol. 191, No. 3, pp. 557-563.

Spieles et al., "An Attempt to Recover Viable Human Red Blood Cells after Freeze-Drying," Cryo-Letters, 1996, vol. 17, pp. 43-52.

Spieles et al., "The effect of storage temperature on the stability of frozen erythrocytes," Cryobiology 32(4):366-378 (1995), Abstract.

Stadler et al., "Influence of Cold Storage Altered Red Cell Surface on the Function of Platelets," Journal of Medicine, 1994, vol. 25, No. 6, pp. 353-361.

Valeri, C.R., "Simplification of the Methods for Adding and Removing Glycerol During Freeze-Preservation of Human Red Blood Cells

(56) References Cited

OTHER PUBLICATIONS with the High or Low Glycerol Methods: Biochemical Modification Prior to Freezing," Transfusion, 1975, vol. 15, pp. 195-218.

Valeri, R. et al., "A Simple Method for Freezing Human Platelets Using 6% Dimethylsulfoxide and Storage at -80° C." Blood 1974, vol. 43 No. 1, pp. 131-136.

Walper et al., "Preservation of Resuspended Red Cell Concentrate, Analysis of Purines, Nucleosides and Nucleotides in Stored Red Cells," Folia Haematologica (Leipzig), 1987, vol. 114, No. 4, pp. 463-464.

Watts et al., "Comparison of the Protective Effects of Verapamil, Diltiazem, Nefedipine, and Buffer Containing Low Calcium upon Global Myocardial Ischemic Injury," J. Mol. Cell Cardiol. 18:255-263 (1986).

Winter et al., "2,4-Dinitrophenol and Carbonylcyanide p-Trifluoromethoxyphenylhydrazone Activate the Glutathione S-Conjugate Transport ATPase of Human Erythrocyte Membranes," Archives of Biochemistry and Biophysics, 1994, vol. 314, No. 1, pp. 17-22.

Zachara B., "The Effect of Persantin on the Phosphate Compounds in Erythrocytes During Blood Conservation," Acta. Haemat, 1972, vol. 48, pp. 164-175.

Zachara et al., "Inorganic Phosphate, Potassium and Sodium in Erythrocytes and in Plasma of Blood Conserved in the Presence of Adenosine and Diphyridamole," Abh. Akad. Wiss. DDR, 1975, pp. 467-471.

Zhao et al., "Maintenance of Cation Gradients in Cold-Stored Erythrocytes . . . Amiloride," Cryobiology, 1989, vol. 26, pp. 132-137.

\* cited by examiner

COMPOSITION FOR CRYOPRESERVATION COMPRISING NICOTINAMIDE, GLYCEROL AND RED BLOOD CELLS

This application is a divisional of, and claims the benefit of priority of, application Ser. No. 11/334,950 filed Jan. 18, 2006 now abandoned, which is a continuation of, and claims the benefit of priority of, U.S. application Ser. No. 09/623,846, filed Sep. 7, 2000 now abandoned, which was a U.S. National Phase Application of International Application No. PCT/US99/11674, filed May 26, 1999, which claimed priority of U.S. Provisional Application No. 60/086,836, filed May 26, 1998, all of which are incorporated by reference herein.

BACKGROUND OF THE INVENTION

Blood is composed of plasma and cellular constituents and plays a prominent role in several key physiological systems of the human body, including immunology, hemostasis, and tissue oxygenation. Movement of the respiratory gases oxygen ($O_2$) and carbon dioxide ($CO_2$) is the chief function of erythrocytes or red blood cells. This facilitated movement of $O_2$ and $CO_2$ is carried out by hemoglobin, an iron-containing, multi-subunit protein contained within red blood cells. The necessity for encapsulating hemoglobin within the red blood cell is twofold. First, hemoglobin has very specific binding parameters to ensure delivery of these critical molecules to the proper sites. By regulating the concentration of cofactors and free ions, the red blood cell provides the proper environment for optimum uptake and release of $O_2$. Secondly, free heme has toxicity effects on both the renal and hepatic systems and can lead to conditions such as hemoglobinuria.

The red blood cell structural components which confine the hemoglobin are comprised of the membrane bilayer and the cytoskeleton. The membrane itself contains choline and amino phospholipids, cholesterol, and integral membrane proteins. Along the inner surface of the membrane lies the cytoskeleton. This mesh-like skeleton is composed of long, filamentous spectrin molecules joined together at foci of F-actin and protein 4.1 complexes. This cytoskeletal mesh is linked to the membrane through protein-protein interactions such as the ankyrin/protein 4.2 mediated connection of spectrin and the integral membrane protein Band 3, and possibly via direct protein-lipid interactions. Through these connections, the cytoskeleton provides the red blood cell its stability and shape. In the absence of proper binding within the cytoskeletal mesh or the connection of the cytoskeleton to the membrane, a critically weakened red blood cell results. Several human diseases have been identified stemming from either an absence of a specific protein or a defective protein interaction. Most of these defects lead to morphologically abnormal red blood cells and severe hemolytic anemias.

A wide variety of injuries and medical procedures require the transfusion of whole blood or a variety of blood components. Blood transfusions are routinely used to increase oxygen delivery capacity and circulatory volume in patients. Safe, quick, and easy access to transfusable red blood cell units is not only important for trauma victims with massive blood loss, but also for patients undergoing elective surgery or who have diseases, such as several types of hereditary hemolytic anemias, which result in a loss of circulating red blood cells. The ability to store red blood cells for extended time periods ensures that a supply of transfusable red blood cells will be available when needed. Potential uses include storage of unique serotypes, units intended for autologous transfusion and stockpiling general blood types for emergency situations. Limitations in the current storage methodologies have led, in part, to occasional shortages of blood supply, resulting in postponement of elective surgeries and calls for donations from blood banks and hospitals.

Currently, two methods are approved for extended storage of red blood cells. The majority of red blood cell units are stored in citrate phosphate-dextrose at 4° C. For example, when donor blood is received at a processing center, erythrocytes are separated and stored by various methods, generally as a unit of packed erythrocytes having a volume of from 200 to 300 ml and a hematocrit value of 70 to 90. However, due to metabolic depletion and subsequent physical degradation, these cells may be stored no longer than 42 days. Furthermore, while 70% of these stored cells remain in circulation following transfusion, true $O_2$ delivery capability has not been demonstrated.

During storage, human red blood cells undergo morphological and biochemical changes, including decreases in the cellular level of adenosine triphosphate (ATP) and 2,3-diphosphoglycerate (2,3-DPG), changes in cellular morphology, and progressive hemolysis. The concentration of ATP, after a brief initial rise, progressively declines to between 30 and 40% of its initial level after six weeks of storage. Morphological changes occur during storage, ultimately leading to the development of spicules which can bud off as vesicles, radically changing the surface-to-volume ratio of the cells and their ability to deform on passing through narrow channels. The fluidity of the cell membrane of red cells, which is essential for the passage of red cells through the narrow channels in the spleen and liver, is loosely correlated with the level of ATP. The concentration of ATP and the morphology of red cells serve as indicators of the suitability of stored cells for transfusion.

The second method is frozen storage at −80° C. using 40% (w/v) glycerol as a cryoprotectant. However, this additive penetrates the membranes of many biological cells and possesses unwanted properties when infused into humans. While this method can be used for up to 10 years of storage, the glycerol must be washed out prior to transfusion. The washing procedure utilizes costly equipment and is time and labor intensive. Additionally, a significant level of hemolysis (10-15% typically) occurs during the wash procedure. Finally, since this procedure is also considered to compromise the sterility of the red blood cell units, post-wash storage is significantly limited. Consequently, this method of storage is only used for blood with extremely rare factor types and autologous and directed donation units which will not be used within a 42 day period. As of 1992, the most recent data available, approximately 14% (nearly 2 million units) of the available supply of transfusable red blood cells were discarded. The ability to cryopreserve red blood cells without the added expense and time of washing, or at least reducing the number of washing cycles necessary, would enable salvage of a significant percentage of these discarded units, thereby providing a further buffer against blood product is shortages.

Current theories of red blood cell cryopreservation consider ice formation and propagation to be the primary, if not the sole factor affecting cell recovery and viability following storage. Consequently, investigation of methods to cryopreserve red blood cells only consider slight variations of traditional cryoprotectant methodologies. Prior methods for the preservation, storage, and transfusion of red blood cells are explained in Horn, Sputtek, Standl, Rudolf, Kuhnl, and Esch, *Transfusion of Autologous, Hydroxyethyl Starch-Cryopreserved Red Blood Cells*, Anesth. Analg. 1997; 85; 739-745. However, temperature-induced modulation of cellular biochemistry is a well recognized phenomenon by experts in this field. The descriptions herein provide methods of utilizing the red blood cell biochemistry to overcome cold-induced imbalances which would normally lead to cellular hemolysis following cryopreservation. Through these methods, the level of non-specific cryoprotection against ice formation may be reduced.

Two general procedures are currently available for the frozen preservation of living cells in terms of the cryoprotectant used. One utilizes the addition of high concentrations of low molecular weight penetrant solutes. Due to toxicity and osmotic problems, specialized equipment and techniques are required to remove the solutes following thawing. The second utilizes high molecular weight polymers which do not enter the cells. Post-thaw processing in this case is logistically simpler but storage must be at very low temperature, typically in liquid nitrogen. The formation of ice, which is a prime concern in any method of cell cryopreservation, is initiated by ice crystal nuclei. As the temperature falls and water crystallizes to ice, the cell is progressively dehydrated and at some point cell injury results. The nature of the dehydration injury is believed to be the result of membrane stresses leading to membrane rupture. This form of injury can be prevented by the addition of solutes at a multi-molar concentration so that the amount of ice formed is insufficient to result in damaging cell dehydration.

For many years it has been known that certain molecules may be cryoprotective. It is necessary for these penetrating cryoprotectants to reduce the amount of extracellular ice formed and thereby reduce cell dehydration, while at the same time increasing the intracellular concentration to make intracellular crystallization less likely. Such a solute, to be useful, must be non-toxic at high concentration and must freely penetrate the cell. Both glycerol and dimethylsulfoxide (DMSO) have been used for this purpose. Glycerol is remarkably non-toxic at high concentrations but penetrates cell membranes slowly and is therefore difficult to introduce and remove. Dimethylsulfoxide penetrates rapidly but becomes increasingly toxic as concentrations exceed 1M (about 7%). Large molecular weight polymers, such as polyvinylpyrrolidone (PVP), dextran, and more recently hydroxyethyl starch (HES), do not enter the cell, and the mechanism by which they confer cryoprotection has been the subject of speculation.

As stated above, in order to prolong the storage of red blood cells it is necessary to store the cells or treat them in some manner that prevents a decline in ATP, and, if possible, 2,3-diphosphoglycerate (2,3-DPG), in addition to protection against ice crystal damage. Typically, such solutions contain phosphate, glucose, and adenine which function to prolong shelf-life by maintaining the level of ATP in the cells. In addition, glycolytic activity is enhanced in red blood cells if the intracellular pH measured at 4° C. is about 7.4 The effective osmolality of the suspending solution is another factor of importance in extending red cell storage time. It has been shown that hypotonically induced increases in mean cell volume substantially reduce hemolysis and improves red cell morphology during storage. Although the mechanism has not been proven, it is possible that osmotic swelling increases cell surface tension, thereby opposing the shape changes usually associated with stored red cells. Although the hypotonicity of the additive solution is limited by the danger of hemolysis during the addition of the solution, red cells, which are normally bi-concave disks, can swell to nearly twice their normal volume at an external osmolality of approximately 170 mOsm before they hemolyze. If the additive solution is too hypotonic, the red cells will burst (hemolyze). As a result, solutions that are too hypotonic cannot be used. While maintenance of ATP and 2,3-DPG are generally thought of with reference to 4° C. storage, maintaining the concentration of these metabolites is important for post-thaw storage. For the effects on ATP levels, hemolysis, potassium leakage, and shedding of microvesicles, on the maintenance and storage of red blood cells, see Greenwalt, Rugg, and Dumaswala, *The Effect of Hypotonicity Glutamine, and Glycine on Red Cell Preservation*, Transfusion 1997; 37; 269-276.

The goal of extended red blood cell storage is to maintain the metabolic and morphologic characteristics so that the in vivo parameters (oxygen delivery capacity and circulatory half-life) are comparable to fresh, non-frozen red blood cells. Additionally, the level of hemolysis during the storage cycle must remain within acceptable levels to allow direct transfusion of the thawed red blood cell unit without complications from hemoglobin toxicity. These goals can be accomplished using the method of this invention. The method described herein provides the advantages of both currently approved storage methods—extended storage time in the frozen state and immediate availability as in refrigerated storage.

Hospitals and blood banks would greatly benefit from a directly-transfusable frozen red blood cell product. Most current investigational approaches to accomplish this attempt to merely replace glycerol with a non-toxic, transfusable cryoprotectant. However, results have shown that most cryoprotectants need to be used at concentrations which may not be transfused or their protective qualities are not enough to maintain hemolysis at acceptable levels for transfusion. Additionally, most procedures require storage at −193° C. in liquid nitrogen vapor. This would be expensive and difficult to incorporate into current blood banking procedures, making extended storage at temperatures below −80° C. impractical.

The invention described herein addresses the noted problems of storage, morphological changes, metabolic changes, and long term functional effectiveness of red blood cells. Further, the present invention achieves unexpected and surprising results in the preservation of red blood cells through treating with the compositions and methods of this invention and which previously would have been considered impossible.

SUMMARY OF THE INVENTION

This invention provides a method for storing red blood cells in the frozen state at subzero temperatures (−10° to −193° C.) such that the resulting thawed red blood cell unit contains viable cells. Specifically, this is accomplished through a combination of biochemical stabilization and cryoprotectant solution. A biochemical stabilizing reagent is one that provides no traditional cryoprotection, in that it alone does not diminish the formation or quantity of ice during the freezing process at the concentration used. In the event that the combined cryoprotectant solution is composed of transfusable cryoprotective reagents, the resulting thawed red blood cell unit is directly transfusable. In all circumstances, incorporating biochemical stabilizing technology allows cryopreservation of red blood cells utilizing concentrations of cryoprotectants lower than would be necessary in the absence of biochemical stabilization.

Biochemical stabilization involves the addition of reagents which target specific red blond cell components and biochemical pathways susceptible to damage during the freeze/thaw cycle. Stabilization with these reagents renders the cells partially resistant to freeze/thaw-induced damages, which ultimately results in hemolysis. Biochemical stabilization may be targeted to maintain metabolic components, antioxidant potential, intracellular ionic distribution, membrane fluidity, and integrity of the cytoskeletal structure. Additionally, specific second messenger pathways, such as the cyclooxygenase, lipoxygenase, hexose monophosphate and phosphorylation pathways, may be manipulated directly by biochemical reagents or indirectly through regulation of specific messenger molecules, including cyclic-adenosine monophosphate (c-AMP), cyclic-guanine monophosphate (c-GMP), intracellular calcium, inositol triphosphate, and diacylglycerol.

More specifically, a single reagent or combination of reagents may be added to red blood cell units to target each of the above items. For example, reagents can be added to maintain or enhance intracellular concentrations of ATP such as glucose, pyruvate or inorganic phosphate as well as blocking ATP-depleting ATPases such as amiloride mediated inhibition of the $Na^+/H^+$ exchanger. Preventing oxidative damage to the membrane or hemoglobin may be accomplished through the addition of antioxidants such as glutathione, tocopherol, ascorbate and bioflavonoids as well as through the stimulation of the hexose monophosphate pathway by ribose. Ionic distribution can be regulated through activation or inhibition of specific ion pumps. Calcium may be controlled with nifedipine or verapamil while amiloride will effect sodium regulation as mentioned above. Further potassium and chloride ionic distribution may be maintained through inhibition of the $K^+/Cl^-$ co-transporter with bumetanide. The cyclooxygenase and lipoxygenase pathways may be regulated through the addition of flurbiprofen, dipyridamole, or aspirin while phosphorylation events can be manipulated through inhibition by kinase inhibitors such as H7 (1-[5-isoquinolinylsulfonyl]-2-methylpiperazine), staurosporin, or chelerythrine or stimulated by diacylglycerol palmitoyl carnitine. Membrane stabilization and fluidity is controlled through the addition of pentoxifylline, nicotinamide or amantadine and cytoskeletal structure may be maintained through actin stabilization by the use of Taxol, $[2aR-[2a\alpha,4\beta,4a\beta,6\beta,9\alpha(\alpha R^*,\beta S^*,11\alpha,-12\alpha,12a\alpha,12b\alpha]]-\beta-(Benzoylamino)-\alpha-hydroxybenzenepropanoic$ acid 6,12b-bis(acetyloxy)-12-(benzoyloxy)-2a,3,4,4a,5,6,9,10,11,12,12a,12b-dodecahydro-4,11-dihydroxy-4a,8,13,-13-tetramethyl-5-oxo-7,11-methano-1H-cyclodeca[3,4]benz-[1,2-b]oxet-9-yl-ester, or cytochalasins or spectrin stabilization with polyamines. Specific cyclic nucleotide regulated second messenger pathways may be activated through the use of adenosine (elevates c-AMP) and sodium nitroprusside or other nitric oxide donors (elevates c-GMP).

In addition to biochemical stabilization, cryoprotectants are used to protect the red blood cell unit from damage by ice crystal formation during the freeze/thaw cycle. The cryoprotectants may be used individually or as mixtures made up of penetrating and/or non-penetrating compounds. Examples of potential cryoprotectants include, but are not limited to dimethylsulfoxide, polyvinyl pyrrolidone, dextran, maltodextrins, 2,3-butanediol, hydroxyethyl starch, polyethylene glycol and glucose and other carbohydrates.

In one embodiment for preserving human red blood cells the method includes drawing a volume of packed red blood cells in ADSOL, a currently licensed additive solution sold by Baxter Travenol, using standard blood banking protocols. The ADSOL is removed by centrifugation, and a volume of preservation solution containing the desired cryoprotectants and any additional biochemical reagents is added. The red blood samples containing cryoprotectants are submerged in liquid nitrogen for freezing and immediately transferred to a $-80°$ C. freezer for extended storage. Biochemical stabilization may be targeted to maintain metabolic components, antioxidant potential, intracellular ionic distribution, membrane fluidity and integrity of cytoskeletal structure. Additionally, specific second messenger pathways, such as the cyclooxygenase, lipoxygenase, hexose monophosphate and phosphorylation pathways, may be manipulated directly by biochemical reagents or indirectly through regulation of specific messenger molecules, including c-AMP, c-GMP, intracellular calcium, inositol triphosphate, and diacylglycerol. In one preferred embodiment the biochemical reagents are present in a concentration so as to prevent the hemolysis of the red blood cells during the freeze/thaw cycle and even more preferably have concentrations of about 500 μM nifepipine, about 20 μM cytochalasin B, about 500 μM Taxol, about 5 mM pentoxifylline, and about 25 μg/ml flurbiprofen. The biochemical reagents are present in 2.5% DMSO as a carrier agent. All conditions contain 7.5% dextran (Dex; 40,000 MW), 2% polyvinyl pyrrolidone (PVP; 40,000 MW), 5% hydroxyethyl starch, and 5% polyethylene glycol. The low, transfusable concentrations of cryoprotectants can work in combination to protect the red blood cells during cryopreservation better than any single cryoprotectant alone. Moreover, the addition of the reagents and the biochemical modulation with the low concentrations of transfusable cryoprotectants works in combination to further protect the red blood cells during cryopreservation. An alternative method is to add the isotonic saline or preservative solution containing the biochemical reagents and a volume of Glycerolyte 57 (Fenwall), preferably about 20% glycerol and freeze the bags at $-80°$ C. The additives used include nicotinamide, nikethamide, nifedipine, pentoxifylline, and flurbiprofen. The 20% glycerol with the addition of the biochemical additives reduces the level of hemolysis and meets the criteria for a transfusable blood unit based on the overall hemolysis and residual free hemoglobin levels.

Thus, one embodiment of the present invention is a red blood cell storage composition including a red blood cell composition and a composition of biochemical stabilization reagents. In such an embodiment the biochemical reagents should be present at a concentration so as to permit decreased hemolysis during the freeze-thaw cycle and increased in vitro functional activity when compared to red blood cells preserved under the same conditions but in the absence of the biochemical reagents.

In yet another embodiment of the present invention, a red blood cell composition is formed comprising red blood cells, a composition of red blood cells and biochemical reagents, and a combination of one or more cryoprotective agents.

Another embodiment is directed to a human red blood cell composition comprising human red blood cells, a composition of red blood cells and biochemical reagents. Reagents can be added to maintain or enhance intracellular concentrations of ATP such as glucose, pyruvate or inorganic phosphate as well as blocking ATP-depleting ATPases such as amiloride inhibition of the $Na^+/H^+$ exchanger. Preventing oxidative damage to the membrane or hemoglobin may be accomplished through the addition of antioxidants such as glutathione, tocopherol, ascorbate and bioflavonoids as well as through the stimulation of the hexose monophosphate pathway by ribose. Ionic distribution can be regulated through activation or inhibition of specific ion pumps. Calcium may be controlled with nifedipine or verapamil while amiloride will effect sodium regulation as mentioned above. Further potassium and chloride ionic distribution may be maintained through inhibition of the $K^+/Cl^-$ co-transporter with bumetanide. The cyclooxygenase and lipoxygenase pathways may be regulated through the addition of flurbiprofen, dipyridamole, or aspirin while phosphorylation events can be manipulated through inhibition by kinase inhibitors such as H7 (1-[5-isoquinolinylsulfonyl]-2-methylpiperazine), staurosporin, or chelerythrine or stimulated by diacylglycerol palmitoyl carnitine. Membrane stabilization and fluidity is controlled through the addition of pentoxifylline, nicotinamide or amantadine and cytoskeletal structure may be maintained through actin stabilization by the use of TAXOL or cytochalasins or spectrin stabilization with polyamines. Specific cyclic nucleotide regulated second messenger pathways may be activated through the use of adenosine (elevates c-AMP) and sodium nitroprusside or other nitric oxide donors (elevates c-GMP). The biochemical reagents are present in a concentration so as to prevent the hemolysis of the red blood cells during the freeze/thaw cycle.

DESCRIPTION OF ILLUSTRATIVE EMBODIMENTS

The biochemical stabilization of this invention is based on the application of specific effectors, which target specific aspects of cellular biochemistry to protect cells against specific modes of damage. The method of cryopreservation is such that the stored cells may be directly transfused following thaw, by combining biochemical reagents and low concentrations of transfusable cryoprotectants. The biochemical stabilization involves regulation of the metabolic, ionic, cytoskeletal, and membrane component, rendering the treated red blood cells less susceptible to damage induced during freezing and thawing at temperatures between $-10°$ C. to $-193°$ C.

In one embodiment, specific cellular effectors are nifedipine, cytochalasin B, Taxol, pentoxifylline, flurbiprofen, nikethamide, ribose, and trehalose. These modifiers are added to the packed red blood cells and the preservative solution. Each of the modifiers affects different specific cellular biochemistry. In one aspect of the present invention, nifedipine an inhibitor acting through the calcium cascade controls calcium, while, cytochalasin B and Taxol are cytoskeletal modifiers and provide stabilization to the cell through actin stabilization. In another aspect of the present invention, membrane stabilization and fluidity may be controlled through pentoxifylline, a membrane modifier. Ribose is added to prevent oxidative damage to the cell by stimulation of the hexose monophosphate pathway.

The second messenger effectors have been demonstrated to provide biochemical stabilization to the red blood cells either individually or in combination with others. More, importantly, the addition of these reagents allows biochemical modulation to enhance cryoprotection at lower glycerol concentrations which normally result in nearly 100% of the red blood cells being inadequately protected during the freeze/thaw and washing cycles. In describing the chemicals which have shown utility as effectors of the second messenger pathways, it must be understood that the actual chemicals mentioned together with functionally equivalent materials are intended to be within the scope of this invention. Chemicals that are known to applicants to have known or demonstrated utility as modifiers have been specifically set forth in the instant application. However, it is intended that the scope of the application be extended to other functionally effective chemicals, both existing chemicals and chemicals yet to be discovered.

Certain chemicals which are thought to be functionally equivalent materials for the modifier acting through the second messenger pathway are those selected from cyclic-adenosine monophosphate, c-(AMP), cyclic-guanine monophosphate, c-(GMP), intracellular calcium, inositol triphosphate, and diacylglycerol. Functionally equivalent modifiers acting through the cyclic nucleotide regulated second messenger pathway are those selected from adenosine, sodium nitroprusside, and other nitric oxide donors. Materials thought to be functionally equivalent to the modifier of intracellular concentrations of ATP are those selected from glucose, pyruvate, and inorganic phosphate, as well as ATP-depleting ATPases such as amiloride. Preventing oxidative damage to the membrane or hemoglobin may be accomplished through the addition of functionally equivalent antioxidants such as glutathione, tocopherol, ascorbate and bioflavonoids as well as through the stimulation of the hexose monophosphate pathway by ribose. Ionic distribution can be regulated through activation or inhibition of specific ion pumps. Functionally equivalent modifiers of calcium may be selected from nifedipine or verapamil while amiloride will effect sodium regulation as mentioned above. Further potassium and chloride ionic distribution may be maintained through inhibition of the $K^+/Cl^-$ co-transporter with bumetanide. The cyclooxygenase and lipoxygenase pathways may be regulated through the addition of functionally equivalent modifiers of flurbiprofen, dipyridamole, or aspirin while phosphorylation events can be manipulated through inhibition by kinase inhibitors such as H7 (1-[5-isoquinolinylsulfonyl]-2-methylpiperazine), staurosporin, or chelerythrine or stimulated by diacylglycerol palmitoyl carnitine, which are also functionally equivalent reagents. Reagents which are functionally equivalent regulators of membrane stabilization and fluidity are pentoxifylline, nicotinamide or amantadine; while for the regulation of cytoskeletal structure through actin stabilization, the reagents are TAXOL or cytochalasins and for spectrin stabilization, polyamines. Specific cyclic nucleotide regulated second messenger pathways may be activated through the use of functionally equivalent adenosine (elevates c-AMP) and sodium nitroprusside or other nitric oxide donors (elevates c-GMP).

The post-thaw life of the red blood cells after cryopreservation may be successfully extended by storing the cells at $-80°$ C. with the biochemical reagents of this invention. When red blood cells were stored for 3-7 days in a $-80°$ C. freezer and thawed at $37°$ C. in a water bath and analyzed for post-storage hemolysis, as compared to red cells stored in glycerol concentrations alone, the percentage of hemolysis was as follows: 14.36% with nifedipine, 15.01% with Taxol and cytochalasin B, 11.46% with nifedipine, pentoxifylline, and flurbiprofen, and 11.66% with nifedipine, cytochalasin, and Taxol. These results compare favorably to enhance cryoprotection when compare to glycerol concentrations which normally result in nearly 100% of the red blood cells being inadequately protected during the freeze/thaw and washing cycles. To perform the experiment, a packed red blood cell unit in ADSOL was obtained using standard blood banking protocols. The ADSOL was removed by centrifugation and a volume of preservation solution containing the desired cryoprotectants and biochemical reagents was added. The final concentrations of cryoprotectant used were 7.5% dextran, 2% polyvinyl pyrrolidone, 5% hydroxyethyl starch, and 2.5% dimethyl sulfoxide as a biochemical reagent carrier. Reagents used included 500 μM nifedipine, 20 μM cytochalasin B, 500 μM Taxol, 5 mM pentoxifylline and 25 μg/ml flurbiprofen. After the ADSOL was removed and the preservation solution was added, 50 ml of red cells was placed into freezing bags having a maximum volume of 150 ml. An equal volume was added to each of the bags. The bags were plunge frozen and stored at $-80°$ C. for 2-7 days and thawed by submersion a $37°$ C. water bath for 10 minutes. Level of thaw hemolysis was determined as the ratio of free hemoglobin to total hemoglobin. This biochemical reagent mixture is able to be directly transfused following storage.

Storing red blood cells at $-10°$ C. to $-193°$ C. requires the addition of a cryoprotective agent, such as dimethyl sulfoxide (DMSO). Cryoprotective agents such as DMSO are polar molecules which penetrates the cell membrane and serves to preserve cell viability during the cryopreservation process. In addition to DMSO, other cryoprotective agents used in this invention include polyvinyl pyrrolidone, dextran maltodextrins, 2,3-butanadiol, hydroxyethyl starch, polyethylene glycol, glucose, and combinations thereof. The success of cryopreservation with certain water soluble molecules which do not permeate the cells has been reported, however, the exact mechanism for this success is unknown. It has been speculated that this phenomenon including that the polymers protect cells by lowering extracellular salt concentrations at subfreezing temperatures just as penetrating cryoprotectants do, or, that the polymers might adsorb to cells and thus protect the membrane in some way. It has also been speculated that during freezing an electrolyte gradient develops from inside to outside the cells causing an electrolyte leakage which relieves osmotic stress. The cryoprotectants may be used individually or as mixtures made up of penetrating and/or non-penetrating compounds in transfusable concentrations to protect the red blood cells from damage by ice crystal formation during the freeze/thaw cycle.

For example, it can be shown by a comparison of the following percentages of thaw hemolysis that combinations of transfusable concentrations of cryoprotectants allow increased protection from hemolysis than a single cryoprotective agent: 7.5% dextran, 11.19% hemolysis; 2% polyvinyl pyrrolidone, 47.39% hemolysis; 5% hydroxyethyl starch, 43.17% hemolysis; 7.5% dextran and 2% polyvinyl pyrrolidone, 6.42% hemolysis; 7.5% dextran and 5% hydroxyethyl starch, 8.56% hemolysis; 2% polyvinyl pyrrolidone and 5% hydroxyethyl starch, 23.46% hemolysis, and finally 7.5% dextran, 2% polyvinyl pyrrolidone, and 5% hydroxyethyl starch, 4.44% hemolysis.

A red blood cell storage composition of the present invention, includes a storage composition, a composition of red blood cells, and a composition of biochemical reagents, the reagents present in a concentration so as to prevent the hemolysis of the red blood cells during the freeze/thaw cycle and in a concentration to increase the in vitro functional activity when compared to red blood cells preserved under the same conditions but in the absence of the biochemical reagents. As the term is used herein and in the claims the "storage composition," is intended to mean a pharmacologically inert fluid into which the red blood cells may be suspended and which does not adversely affect the preservation abilities of the compositions disclosed herein, for example physiological saline. Biochemical stabilization may be targeted to maintain metabolic components, antioxidant potential, intracellular ionic distribution, membrane fluidity and integrity of cytoskeletal structure. Additionally, specific second messenger pathways, such as the cyclooxygenase, lipoxygenase, hexose monophosphate and phosphorylation pathways, may be manipulated directly by biochemical reagents or indirectly through regulation of specific messenger molecules, including cyclic-adenosine monophosphate, (c-AMP), cyclic-guanine monophosphate, (c-GMP), intracellular calcium, inositol triphosphate, and diacylglycerol.

In one preferred embodiment the modifiers acting through the second messenger pathway is selected from cyclic-adenosine monophosphate, (c-AMP), cyclic guanine monophosphate, (c-GMP), intracelluar calcium, inositol triphosphate, and diacylglycerol. Reagents can be added to maintain or enhance intracellular concentrations of ATP such as glucose, pyruvate or inorganic phosphate as well as blocking ATP-depleting ATPases such as amiloride inhibition of the $Na^+/H^+$ exchanger. Preventing oxidative damage to the membrane or hemoglobin may be accomplished through the addition of antioxidants such as glutathione, tocopherol, ascorbate and bioflavonoids as well as through the stimulation of the hexose monophosphate pathway by ribose. Ionic distribution can be regulated through activation or inhibition of specific ion pumps. Calcium may be controlled with nifedipine or verapamil while amiloride will effect sodium regulation as mentioned above. Further potassium and chloride ionic distribution may be maintained through inhibition of the $K^+/Cl^-$ co-transporter with bumetanide. The cyclooxygenase and lipoxygenase pathways may be regulated through the addition of flurbiprofen, dipyridamole, or aspirin while phosphorylation events can be manipulated through inhibition by kinase inhibitors such as H7 (1-[5-isoquinolinylsulfonyl]-2-methylpiperazine), staurosporin, or chelerythrine or stimulated by diacylglycerol palmitoyl carnitine. Membrane stabilization and fluidity is controlled through the addition of pentoxifylline, nicotinamide or amantadine and cytoskeletal structure may be maintained through actin stabilization by the use of TAXOL or cytochalasins or spectrin stabilization with polyamines. Specific cyclic nucleotide regulated second messenger pathways may be activated through the use of adenosine (elevates c-AMP) and sodium nitroprusside or other nitric oxide donors (elevates c-GMP).

In another preferred embodiment, the biochemical reagents are: nifedipine in a concentration of about 500 µM, cytochalasin B in a concentration of about 20 µM, Taxol in a concentration of about 500 µM, pentoxifylline in a concentration of about 5 mM, and flurbiprofen in a concentration of about 25 µg/ml. The blood cell storage composition of the present embodiment may further include a cryoprotective agent, the cryoprotective agent being selected from dimethyl sulfoxide, polyvinyl pyrrolidone, dextran maltodextrins, 2,3-butandiol, hydroxyethyl starch, polyethylene glycol, glucose, and combinations thereof. Preferably, the cryoprotective agents are: dextran in a concentration of about 7.5%; polyvinyl pyrrolidone in a concentration of about 2%; dimethyl sulfoxide in a concentration of about 2.5%; hydroxyethyl starch in a concentration of about 5%, and polyethylene glycol in a concentration of about 5%. The prolonged storage of the red blood cells should be carried out at a temperature below the red cells' normal physiological temperature. In one embodiment, the temperature is from about −10 C to about −193° C. In another embodiment the temperature below the red blood cells' normal physiological temperature is about −80° C.

The following examples demonstrate the ability of biochemical stabilization to enhance the preservation of red blood cells at temperatures less than −10° C. Both glycerol-based and transfusable, polymeric-based cryoprotectant solutions are described.

The examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept and scope of the invention.

Example 1

The following example demonstrates the damage induced during the freeze/thaw cycle when the glycerol concentration is decreased. A significant percentage of the hemolytic damage is shown to be reversed by the addition of a preservative solution containing adenine, glutamine, sodium chloride, mannitol, and dextrose, with the essential additive being dextrose, and final concentrations of 5 mM pentoxifylline and 25 µg/ml flurbiprofen in DMSO as a carrier.

Specifically, 50 ml of packed red blood cells was added to a PVC freezing bag with a maximum volume of 150 ml. Isotonic saline or preservative solution containing the additional biochemical reagents pentoxifylline and flurbiprofen was mixed with the red blood cells. A volume of Glycerolyte 57 (Fenwall) was added slowly until the final concentration of glycerol was achieved. The total volume of all additions was 50 ml, making the final concentration of the red blood cell unit 100 ml. The PVC bags were frozen at −80° C. for 2-7 days and thawed by submersion in a 37° C. water bath for 10 minutes. The level of thaw hemolysis was determined as the ratio of free hemoglobin to total hemoglobin. The levels of thaw hemolysis are shown below in TABLE 1.

TABLE 1

LEVELS OF THAW HEMOLYSIS

|  | % Hemolysis |
|---|---|
| 40% Glycerol | 1.91 |
| 30% Glycerol | 3.53 |
| 20% Glycerol | 35.29 |
| 20% +Additives | 14.87 |

These results confirm the loss of red blood cell protection at reduced glycerol concentrations and the ability of biochemical reagents to provide cryoprotection at glycerol concentrations which alone are unable to completely protect red blood cells during cryopreservation.

Example 2

The following example further demonstrates the damage induced during the freeze/thaw cycle when the glycerol concentration is decreased, after red blood cells are frozen and stored at −80° C. Fifty ml of packed red blood cells were added to a PVC freezing bag. Isotonic saline or preservative solution containing the additional biochemical reagents of interest was mixed with the red blood cells. The samples were treated as follows prior to freezing at −80° C.:
1. 40% Glycerol
2. 20% Glycerol
3. Nicotinamide
4. Nikethamide, Nifedipine
5. Nikethamide, Nifedipine, Pentoxifylline, Flurbiprofen
6. Nicotinamide Nikethamide, Nifedipine, Pentoxifylline, Flurbiprofen A volume of Glycerolyte 57 (Fenwall) was added slowly until the final concentration of glycerol was achieved. The total volume of all additions was 50 ml, making the final volume of the red blood cell unit 100 ml. The PVC bags were frozen at −80° C. for 2-7 days and thawed by submersion in a 37° C. water bath for 10 minutes. The level of thaw hemolysis was determined as the ratio of free hemoglobin to total hemoglobin. Additionally, the glycerol was removed from the thawed red blood cell units by serial dilution with saline similar to blood bank protocols. The overall hemolysis and the final residual free hemoglobin levels were also determined.

TABLE 2 compares 40% glycerol to 20% glycerol and 20% glycerol with the indicated additives. The additives used included nicotinamide, nikethamide, nifedipine, pentoxifylline, and flurbiprofen. The results of 20% glycerol with all additives meet the criteria for a transfusable blood unit based on the overall hemolysis and residual free hemoglobin levels. These results confirm the loss of red blood cell protection at reduced glycerol concentrations and the ability of biochemical reagents to provide cryoprotection at glycerol concentrations which alone are unable to completely protect red blood cell during cryopreservation.

TABLE 2

Biochemical Stabilization with Glycerol Based Cryoprotectant

| Condition | Thaw | Hemolysis (%) Overall | Final |
|---|---|---|---|
| 40% Glycerol | 2.01 | 14.1 | 0.45 |
| 20% Glycerol | 9.39 | 41.48 | 1.09 |
| Nicotinamide | 8.13 | 22.93 | 0.43 |
| Nikethamide/Nifedipine | 9.65 | 37.23 | 0.8 |
| Nikethamide/Nifedipine Pentoxifylline/Flurbiprofen | 9.94 | 34.48 | 0.69 |
| Nicotinamide Nikethamide/Nifedipine Pentoxifylline/Flurbiprofen | 9.07 | 17.84 | 0.33 |

Example 3

The following experiment demonstrates the ability of biochemical addition to provide protection against damage during cryopreservation. The model used is a reduced glycerol cryopreservation system. 10% (w/v) glycerol is added to the unit prior to freezing at −80° C. A significant level of hemolysis occurs so that protection by the added reagent may be distinguished.

A single unit of packed red blood cells in ADSOL was obtained using standard blood banking protocols. The ADSOL was removed by centrifugation and a volume of preservation solution was added until the resulting hematocrit was about 50%. From this red blood cell unit 50 ml of red cells was placed into each of 3 PVC freezing bags having a maximum volume of 150 ml. An equal volume (50 ml) was added to each of the bags composed of the above preservation solution and the experimental conditions. The final composition of the first bag was 10% (w/v) glycerol. The second contained 10% (w/v) glycerol and 2.5% DMSO and 500 µM nifedipine. The bags were frozen at −80° C. for 2-7 days and thawed by submersion in a 37° C. water bath for 10 minutes. The level of thaw hemolysis was determined as the ratio of free hemoglobin to total hemoglobin. Additionally, the glycerol was removed from the thawed red blood cell units by serial dilution with saline similar to blood bank protocols. The overall hemolysis was also determined. The results are shown below in TABLE 3.

TABLE 3

OVERALL HEMOLYSIS

| | % Hemolysis | |
|---|---|---|
| | Thaw | Overall |
| 10% Glycerol | 61.71 ± 1.26 | 93.62 ± 1.28 |
| w/2.5% DMSO | 59.45 ± 0.90 | 81.86 ± 2.72 |
| w/500 µM Nifedipine | 55.12 ± 1.58 | 70.94 ± 2.96 |

This example further confirms the ability of biochemical modulation to enhance cryoprotection at glycerol concentrations which normally result in nearly 100% of the red blood cells being inadequately protected during the freeze/thaw cycles.

Example 4

This example demonstrates the ability of biochemical stabilization to enhance red blood cell cryopreservation in conjunction with a glycerol based cryoprotectant. An aliquot of blood was transferred to a PVC storage bag, to which any experimental agents were added. Glycerol was then added until the desired final glycerol was achieved. This unit was frozen at −80° C., stored and thawed in a 37° C. water bath for 10 minutes. The glycerol was removed by serial dilution and centrifugation with 12%, 1.6% and 0.9% saline until the residual free hemoglobin is less than 2% of the total hemoglobin content.

TABLE 4 show results following the desired procedure. The values indicate the percent hemolysis in the thawed sample, the overall amount of hemolysis following the wash and the is percent of residual free hemoglobin in the final sample. Hemolysis is calculated as the ratio of free hemoglobin to the total hemoglobin content in the sample.

TABLE 4

BIOMEDICAL STABILIZATION WITH
GLYCEROL-BASED CRYOPROTECTANT

| Condition | % Hemolysis | |
|---|---|---|
| | Thaw | Overall |
| 40% Glycerol | 1.9 | 6.1 |
| 20% Glycerol with Control | 37.9 | 52.0 |
| 20% Glycerol with Pentoxifylline | 20.6 | 27.6 |
| 20% Glycerol with Nifedipine | 20.2 | 38.5 |
| 20% Glycerol with Amiloride | 23.6 | 58.7 |
| 20% Glycerol with Flurbiprofen | 22.9 | 46.9 |
| 20% Glycerol with Pentoxifylline Flurbiprofen | 12.5 | 19.3 |
| 20% Glycerol with Nikethamide | 11.0 | 17.0 |
| 20% Glycerol with Nicotinamide | 4.2 | 7.8 |
| 20% Glycerol with Nikethamide Nifedipine Nicotinamide | 7.8 | 14.0 |

Example 5

The following example demonstrates that biochemical stabilization using non-cryoprotective reagents reduces the level of hemolysis when using alternative polymeric reagents as the primary cryoprotectants, when red blood are plunge frozen and subsequently stored at −80° C. A volume of packed red blood cell was mixed with an equal volume of preservation solution containing the desired cryoprotectants and any additional biochemical reagents. The final concentrations of cryoprotectants used were 7.5% dextran (Dex; 40,000 MW) and 2% polyvinyl pyrrolidone (PVP; 40,000 MW). The red blood cell samples containing cryoprotectants were submerged in liquid nitrogen for 3 minutes to freeze and immediately transferred to a −80° C. freezer for extended storage. Following storage for 3-7 days, the samples were thawed at 37° C. in a water bath, and the level of thaw hemolysis was determined as the ratio of free hemoglobin to total hemoglobin. Additionally, the glycerol was removed from the thawed red blood cell units by serial dilution with saline similar to blood bank protocols. The overall hemolysis and the final residual free hemoglobin were also determined.

TABLE 5 shows the biochemical stabilization with a polymeric based cryoprotectant and the resulting percent hemolysis. All samples contained 7.5% Dex and 2% PVP, 2.5% dimethyl sulfoxide as a biochemical carrier, prior to storage at −80° C., in addition to the indicated additive as follows:
1. DMSO
2. Nifedipine
3. Cytochalasin, Taxol
4. Nifedipine, Pentoxifylline, Flurbiprofen
5. Nifedipine, Cytochalasin, Taxol Reagents used include 500 µM nifedipine, 20 µM cytochalasin B, 500 µM Taxol, 5 mM pentoxifylline, and 25 µg/ml flurbiprofen in several combinations.

This example further confirms the ability of biochemical modulation to enhance cryoprotection at glycerol concentrations which normally result in nearly 100% of the red blood cell being inadequately protected during the freeze/thaw and washing cycles. The biochemical stabilization with a polymeric cryoprotectant and resulting percentage hemolysis is displayed in TABLE 5.

TABLE 5

Biochemical Stabilization with
Polymeric Based Cryoprotectant

| Condition | % Hemolysis |
|---|---|
| DMSO | 23.17 ± 0.58 |
| Nifedipine | 14.36 ± 0.45 |
| Cytochalasin/Taxol | 15.01 ± .70 |
| Nifedipine Pentoxifylline/Flurbiprofen | 11.46 ± 0.44 |
| Nifedipine/Cytochalasin/Taxol | 11.66 ± 0.37 |

Example 6

The following example describes an experiment to measure the biochemical stabilization and the post-thaw hemolytic lesion upon dilution, analogous to transfusion, after red blood cell are plunge frozen and stored at −80° C. This type of storage lesion is not commonly addressed but is observed with most non-glycerol based cryoprotective solutions. A volume of packed red blood cell was mixed with an equal volume of preservation solution containing the desired cryoprotectants and any additional biochemical reagents. Using a cryoprotective additive solution (CPA) containing 7.5% dextran (Dex; 40,000 MW) 2% polyvinyl pyrrolidone (PVP; 40,000 MW), 5% hydroxyethyl starch (HES), and 5% polyethylene glycol (PEG), the red blood cell samples containing cryoprotectants were submerged in liquid nitrogen for 3 minutes to freeze and immediately transferred to a −80° C. freezer for extended storage. Following storage the thaw samples were split into two aliquots. The first aliquot was analyzed immediately, and the remaining aliquot was incubated at 4° C. for 3 hours prior to analysis. The analyzed endpoints included hemolysis in the thawed sample and the additional hemolysis which occurs upon 1:1 dilution with one of 2 different diluent solution, PBS or isotype plasma.

In TABLE 6, the stability of the red blood cells following thaw is seen the thaw hemolysis values and the beneficial effect of 4° C. incubation is observed in the dilution induced hemolysis values. Most important is the ability of biochemical additives to enhance the protection during the protocol. The biochemical additives were used to stabilize the cells post-thaw and demonstrate this effect by decreasing the dilution-induces hemolysis. Thus, the damage to the red blood cells during cryopreservation is shown here to be both partially self-reversible and either preventable or correctable with biochemical additions: The treatment conditions were as follows:
1. CPA only
2. CPA+50 mM Ribose
3. CPA+50 mM Ribose
   50 mM Trehalose
   500 µM Nifedipine
   5 mM Pentoxifylline
   50 µg/ml Flurbiprofen

TABLE 6

Biochemical Stabilization Against Post-Thaw Hemolysis

| Condition | | Immediate | | 4° C. | |
|---|---|---|---|---|---|
| | | PBS | Plasma | PBS | Plasma |
| CPA Only | Thaw (%) | | 2.15 | | 2.23 |
| | Dilution (%) | 6.39 | 5.57 | 4.55 | 3.73 |
| CPA + Ribose | Thaw (%) | | 1.62 | | 2.05 |
| | Dilution (%) | 8.94 | 6.60 | 5.85 | 3.85 |
| CPA + All Additives | Thaw (%) | | 2.71 | | 2.56 |
| | Dilution (%) | 3.53 | 3.23 | 2.62 | 2.26 |

Example 7

The following experiment demonstrates the ability of alternative cryoprotectants at low, transfusable concentrations to act in combination to enhance protection against freeze/thaw induced hemolysis.

A single packed red blood cell unit containing ADSOL was obtained and prepared using standard blood banking protocols. The ADSOL was removed by centrifugation and a volume of preservation solution was added. A volume of the resulting red blood cell unit was mixed with an equal volume of preservation solution containing the desired cryoprotectant(s). The final concentrations of cryoprotectants used were 7.5% dextran (Dex; 40,000 MW), 2% polyvinyl pyrrolidone (PVP; 40,000 MW) and 5% hydroxyethyl starch (HES). The red blood cell samples containing cryoprotectants were submerged in liquid nitrogen for three minutes to freeze and immediately transferred to a −80° C. freezer for extended storage. Following storage for 3-7 days, the samples were thawed at 37° C. in a water bath, and the level of thaw hemolysis was determined as described as the ratio of free hemoglobin to total hemoglobin. The levels of thaw hemolysis are shown in TABLE 7 below:

TABLE 7

LEVEL OF THAW HEMOLYSIS

| | % Hemolysis |
|---|---|
| Dex | 11.19 ± 0.38 |
| PVP | 47.39 ± 2.42 |
| HES | 43.17 ± 10.1 |
| Dex/PVP | 6.42 ± 1.38 |
| Dex/HES | 8.56 ± 0.82 |

TABLE 7-continued

LEVEL OF THAW HEMOLYSIS

| | % Hemolysis |
|---|---|
| PVP/HES | 23.46 ± 4.84 |
| Dex/PVP/HES | 4.44 ± 0.04 |

This example confirms that extremely low, transfusable concentrations of cryoprotectants can work in combination to protect red blood cells during cryopreservation better than any single cryoprotectant alone.

In view of the above disclosure, one of ordinary skill in the art should understand and appreciate that one illustrative embodiment of the present invention includes a red blood cell storage composition which includes a composition of red blood cells and biochemistry altering reagents, the biochemistry altering reagents being present at a concentration so as to reduce the percent hemolysis of the red blood cells during the freeze-thaw cycle below that of the percent hemolysis of the red blood cells in the absence the biochemistry altering reagents. Preferably the reagents of the present illustrative embodiment are selected from: modifiers of glycolytic/metabolic components, modifiers of antioxidant potential, effectors of intracellular ionic distribution, modifiers of membrane fluidity, modifiers of cytoskeletal structure, effectors of the cyclooxygenase second messenger pathway, effectors of the lipoxygenase second messenger pathway, effectors of the hexose monophosphate second messenger pathway, effectors of the phosphorylation second messenger pathway, modifiers of the cyclic nucleotide regulated second messenger pathway, and combinations thereof. More preferably, the reagents of the present illustrative embodiment are selected such that: the modifier of glycolytic/metabolic components is selected from glucose, pyruvate, inorganic phosphate, products of the glycolytic pathway such as adenosine triphosphate, nicotinamide adenine dinucleotide, and inhibitors of glycolysis such as iodacetic acid, rotenone, and carbonyl cyanide p-(trifluoromethoxy)-phenyl hydrazine; the modifier of antioxidant potential is selected from glutathione, tocopherol, ascorbate, α-tocopherol, mannitol, bioflavonoids, and derivatives of bioflavonoids including rutin, quercetin, and curcumin; the effector of intracellular ionic distribution acting through the second messenger pathway is selected from nifedipine, nisoldipine, benzamil, glybenclamidediltiazem, clotrimizole, tetramethylammonium diphenylhydantoin, diisothiocyanatstilbene-2,2'-disulfonic acid, verapamil, amiloride, bumetanide, N-(6-aminohexyl)-5-chloro-1-naphthalene sulfonamide and derivatives thereof; the modifier of membrane fluidity is selected from pentoxifylline, nicotinamide, amantadine, carnitine, palmitoyl carnitine, sphingosine, diethylnicotinamide, (nikethamide), nicotinic acid, trehalose, valinomycin, procaine, tetracaine, rimantadine, propanolol, and protease inhibitors such as leupeptin; the modifier of cytoskeletal structure is selected from TAXOL, cytochalasins, paclitaxel, okadaic acid and polyamines such as spermine, spermidine, or putrecine; the effector of the cyclooxygenase and lipoxygenase second messenger pathways is selected from flurbiprofen, dipyridamole, salicyclic acid, and indomethacin; the effector of the hexose monophosphate second messenger pathway is selected from ribose or pyruvate; the effector of the phosphorylation second messenger pathway is selected from H7 (1-[5-isoquinolinylsulfonyl]-2-methylpiperazine), staurosporin, chelerythrine, and diacylglycerol palmitoyl carnitine; and the modifier of the cyclic nucleotide regulated second messenger pathway is selected from adenosine, sodium nitroprusside, dibutyl AMP, dibutyl GMP.

The illustrative composition may also be formulated such that the biochemistry altering reagents are combined with one or more cryoprotective agent. In one preferred embodiment, the cryoprotective agent may be a permanent cryoprotectant, preferably the permanent cryoprotectant may be selected from glycerol, dimethyl sulfoxide, 2,3-butandiol, 1,2-propandiol, 1,3-propandiol, polypropylene glycol, N,N-dimentylacetamide, and 1,3,5-trimethyl pentanetriol and combinations thereof. Alternatively, the composition may be formulated such that the cryoprotective agent is a non-permanent cryoprotectant, which preferably may be selected from hydroxyethyl starch, dextran, polyvinyl pyrrolidone, polyethylene, polyethylene glycol and combinations thereof. A combination of one or more permanent cryoprotectants and one or more non-permanent cryoprotectants may also be utilized in the formulation of the present illustrative embodiment. When the formulation includes a non-permanent cryoprotectant it is preferred that the non-permanent cryoprotectant have a molecular weight of at least about 5,000 MW.

Another illustrative embodiment of the present invention includes a human red blood cell composition including: red blood cells; a storage composition; and a composition of reagents, wherein the composition of reagents is selected from: modifiers of metabolic components, modifiers of antioxidant potential, effectors of intracellular ionic distribution, modifiers of membrane fluidity, modifiers of cytoskeletal structure, effectors of the cyclooxygenase second messenger pathway, effectors of the lipoxygenase second messenger pathway, effectors of the hexose monophosphate second messenger pathway, effectors of the phosphorylation second messenger pathway, modifiers of the cyclic nucleotide regulated second messenger pathway, and combinations thereof.

In such an illustrative composition, it is preferred that: the modifier of glycolytic/metabolic components is selected from glucose, pyruvate, inorganic phosphate, products of the glycolytic pathway such as adenosine triphosphate, nicotinamide adenine dinucleotide, and inhibitors of glycolysis such as iodacetic acid, rotenone, and carbonyl cyanide p-(trifluoromethoxyl)-phenyl hydrazine; the modifier of antioxidant potential is selected from glutathione, tocopherol, ascorbate, α-tocopherol, mannitol, bioflavonoids, and derivatives of bioflavonoids including rutin, quercetin, and curcumin; the effector of intracellular ionic distribution acting through the second messenger pathway is selected from nifedipine, nisoldipine, benzamil, glybenclamidediltiazem, clotrimizole, tetramethylammonium diphenylhydantoin, diisothiocyanatstilbene-2,2'-disulfonic acid, verapamil, amiloride, bumetanide, N-(6-aminohexyl)-5-chloro-1-naphthalene sulfonamide and derivatives thereof; the modifier of membrane fluidity is selected from pentoxifylline, nicotinamide, amantadine, carnitine, palmitoyl carnitine, sphingosine, diethylnicotinamide, (nikethamide), nicotinic acid, trehalose, valinomycin, procaine, tetracaine, rimantadine, propanolol, and protease inhibitors such as leupeptin; the modifier of cytoskeletal structure is selected from TAXOL, cytochalasins, paclitaxel, okadaic acid and polyamines such as spermine, spermidine, or putrecine; the effector of the cyclooxygenase and lipoxygenase second messenger pathways is selected from flurbiprofen, dipyridamole, salicyclic acid, and indomethacin; the effector of the hexose monophosphate second messenger pathway is selected from ribose or pyruvate; the effector of the phosphorylation second messenger pathway is selected from H7 (1-[5-isoquinolinylsulfonyl]-2-methylpiperazine), staurosporin, chelerythrine, and diacylglycerol palmitoyl carnitine; and the modifier of the cyclic nucleotide regulated second messenger pathway is selected from adenosine, sodium nitroprusside, dibutyl AMP, dibutyl GMP.

The illustrative composition may be formulated such that the composition of reagents are combined with one or more cryoprotective agents. In one such illustrative embodiment, the cryoprotective agent is a permanent cryoprotectant selected from glycerol, dimethyl sulfoxide, 2,3-butandiol, 1,2-propandiol, 1,3-propandiol, polypropylene glycol, N,N-dimentylacetamide, 1,3,5-trimethyl pentanetriol and combinations thereof. In another such illustrative embodiment, the cryoprotective agent is a non-permanent cryoprotectant selected from hydroxyethyl starch, dextran, polyvinyl pyrrolidone, polyethylene, polyethylene glycol and combinations thereof. Preferably the cryoprotective solution is a combination of one or more permanent cryoprotectants and one or more non-permanent cryoprotectants. When a non-permanent cryoprotectant is utilized in the formulation, it is preferred that the non-permanent cryoprotectant have a molecular weight of at least 5000 MW.

The illustrative embodiment should be formulated such that the biochemical reagents are present in a concentration so that upon in vitro preservation of the red blood cells at a temperature below the red blood cells normal physiological temperature for a period of about 2-7 days, the red blood cells exhibit decreased hemolysis during a freeze-thaw cycle and increased in vitro functional activity when compared to red blood cells preserved under the same conditions but in the absence of the biochemical reagents. Thus in one preferred embodiment of the present illustrative embodiment the nifedipine has a concentration of about 500 µM, the cytochalasin B has a concentration of about 20 µM, the Taxol has a concentration of about 500 µM, the pentoxifylline has a concentration of about 5 mM, the flurbiprofen has a concentration of about 25 µg/ml, the nikethamide has a concentration of about (1% v/v), the ribose has a concentration of about 0.50 mM, and the trehalose has a concentration of about 50 mM.

It should also be appreciated that the present invention includes a method for storing human red blood cells including: (a) isolating red blood cells from fresh human blood; (b) forming a red blood cell composition; and (c) storing the resulting red blood cell composition at a temperature below normal human physiological temperature effective to preserve the blood cells for a selected period of time. Preferably the red blood cell composition should be formulated so as to include: red blood cells; a storage composition; and a composition of reagents. The composition of reagents should be selected from: modifiers of metabolic components, modifiers of antioxidant potential, effectors of intracellular ionic distribution, modifiers of membrane fluidity, modifiers of cytoskeletal structure, effectors of the cyclooxygenase second messenger pathway, effectors of the lipoxygenase second messenger pathway, effectors of the hexose monophosphate second messenger pathway, effectors of the phosphorylation second messenger pathway, modifiers of the cyclic nucleotide regulated messenger pathway, and combinations thereof. In practicing the present illustrative method, the temperature below normal physiological temperature effective to preserve the red blood cells for selected period of time is preferably about −10° C. to −193° C., and more preferably is about −80° C.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the concept and scope of the invention as defined by the appended claim.

The invention claimed is:

1. A red blood cell composition comprising:
    (a) red blood cells;
    (b) nicotinamide; and
    (c) glycerol at a concentration of about 20% glycerol (weight/volume) and that meets the criteria for transfusable blood based on the overall hemolysis and free hemoglobin levels after freezing and thawing.

2. The composition of claim 1, wherein the nicotinamide and glycerol are present in concentrations so that upon in vitro preservation of the red blood cells at a temperature below the red blood cells' physiological temperature for a period of about 2-7 days, the red blood cells exhibit decreased hemolysis during a freeze-thaw cycle and increased in vitro functional activity when compared to red blood cells preserved under the same conditions but in the absence of nicotinamide.

3. The composition of claim 2, wherein the red blood cells are preserved at a temperature from about −10° C. to about −193° C.

4. The composition of claim 2, wherein the red blood cells are preserved at a temperature of about −80° C.

5. The composition of claim 1, wherein the composition meets the criteria for a transfusable blood unit based on the overall level of hemolysis and residual free hemoglobin levels.

6. The composition of claim 1, further comprising at least one biochemistry altering reagent selected from the group consisting of pentoxyfylline, flurbiprofen, nikethamide, nifedipine, amiloride, taxol, cytochalasin B, trehalose, ribose, a protease inhibitor, a bioflavonoid, and a bioflavonoid derivative.

7. The composition of claim 6, wherein the protease inhibitor is leupeptin.

8. The composition of claim 6, wherein the bioflavonoid derivative is selected from the group consisting of rutin, quercetin, and curcumin.

9. The composition of claim 1, further comprising at least one additional cryoprotective agent selected from the group consisting of dimethyl sulfoxide, 2,3 butanediol, 1,2-propanediol, 1,3-propanediol, polypropylene glycol, N,N-dimethylacetamide, 1,3,5-trimethyl pentanetriol, hydroxyethyl starch, dextran, polyvinyl pyrrolidone, polyethylene, and polyethylene glycol.

10. The composition of claim 1, wherein the composition is frozen.

* * * * *